(12) United States Patent
Polsenski et al.

(10) Patent No.: US 7,041,285 B2
(45) Date of Patent: May 9, 2006

(54) COATINGS WITH ENHANCED MICROBIAL PERFORMANCE

(76) Inventors: Martin J Polsenski, 1808 Montgomery Pl., Jacksonville, FL (US) 32205; Richard I. Leavitt, 404 La Reserve Cir., Ponte Vedra Beach, FL (US) 32082

( * ) Notice: Subject to any disclaimer, the term of this patent is extended or adjusted under 35 U.S.C. 154(b) by 9 days.

(21) Appl. No.: 10/617,177

(22) Filed: Jul. 11, 2003

(65) Prior Publication Data

US 2004/0009159 A1    Jan. 15, 2004

Related U.S. Application Data

(60) Provisional application No. 60/395,330, filed on Jul. 12, 2002.

(51) Int. Cl.
*A61K 54/00* (2006.01)

(52) U.S. Cl. .................................. 424/93.45

(58) Field of Classification Search .......... 424/94.1, 424/94.63; 428/305.5, 317.9, 323, 328, 343, 428/352; 435/74, 170, 180, 183, 200, 252.3, 435/252.33, 262, 264, 274, 320.1; 442/123, 442/347, 361, 378, 394, 413; 536/23.2
See application file for complete search history.

(56) References Cited

U.S. PATENT DOCUMENTS

| | | | |
|---|---|---|---|
| 3,095,307 A | * | 6/1963 | Don et al. ............... 426/8 |
| 3,115,404 A | * | 12/1963 | Carney ..................... 71/6 |
| 4,193,910 A | * | 3/1980 | Rohrbach et al. ........ 523/205 |
| 5,354,603 A | * | 10/1994 | Errede et al. ............ 442/361 |
| 5,919,689 A | | 7/1999 | Selvig et al. |
| 5,998,200 A | | 12/1999 | Bonaventura et al. |
| 6,342,386 B1 | | 1/2002 | Powers et al. |

FOREIGN PATENT DOCUMENTS

WO    WO 01/72911    10/2001

OTHER PUBLICATIONS

Baldwin, E., "Dynamic Aspects of Biochemistry," Cambridge University Press 5th Ed., pp. 1-20 (1967).
Khoury, A., "Prevention and Control of Bacterial Infections Associated with Medical Devices," ASAIO Journal 38, pp. M174-M178 (1992).
International Search Report dated Apr. 29, 2004.

* cited by examiner

*Primary Examiner*—Ralph Gitomer
*Assistant Examiner*—Kailash C. Srivastava
(74) *Attorney, Agent, or Firm*—Finnegan, Henderson, Farabow, Garrett & Dunner, LLP

(57) ABSTRACT

Coatings with enhanced microbial performance can be applied to any surface that is subject to growth of unwanted or undesired organisms. Each layer of the multilayered article may contain microorganisms, enzymes, nutrients and other ingredients that contribute to the microbial performance of each layer and the multilayered article.

25 Claims, No Drawings

COATINGS WITH ENHANCED MICROBIAL PERFORMANCE

This application claims the benefit of U.S. Provisional Application No. 60/395,330, filed Jul. 12, 2002, which is incorporated herein by reference.

It is well known to those skilled in the art that microorganisms, enzymes, and spores can exist, and thrive in many environments. One such environment is that of paints and coatings. Microbiological life can flourish on the wet or uncured surfaces within storage containers and the dry or cured state applied to structures, walls, linings and substrates of every variety. Moreover, layers of microbiological life can form on structures and vessels submerged in water, buried in soil, or immersed in other nutrient sources such as a blood system. To date, those skilled in the art have devoted their efforts and resources to counter some of the negative effects of microorganisms such as mildew growth, corrosion, defacement, and other deterioration. The most common remedy to counter this problem is the use of buffers and biocides to kill the microbiological component involved.

Another aspect of controlling the influence of microorganisms relates to using species of spores, microorganisms, and enzymes as inoculants in a coating. The process of fouling or contamination of a surface commences with the formation of a membrane that enhances settlement of the invading biological or microbiological fouling population. Therefore, an initial step is to identify the target organism for elimination. The next step is the selection of a coating that is compatible with the substrate and provides proper adhesion and endurance. The coating must also be nontoxic to the microorganisms and enzymes that are candidates for addition as an inoculant to the coating. It follows that the selection of the organisms is fundamental to the process. Having identified the target contaminant for elimination, the contaminant's chemical composition is determined. Based upon the chemical composition of the contaminant and the exudate that acts as an adhesive to bond it to the surface, a combination of microbes and enzymes are selected to degrade the effectiveness of the adhesive.

One object of the invention may include production of a dominate natural film or membrane, or a self-sustaining colony, that presents an inhospitable substrate for settlement of the target organism or growth. This film or membrane may be tailored to ensure dominance over other microorganisms likely resident in the paint or coating material. Such embodiments may affect settling organisms prone to modify the settlement surface, i.e., the interface between the surface to be protected and the environment.

Moreover, in the circumstance wherein a structure, vessel, container or article has a surface that is submerged or emersed within a nutrient source, there often begins a film growth that effectively becomes a new substrate. This new substrate enables settlement of a great variety of organisms. Another effect of the invention is to affect this substrate. The most recent advances in the art, U. S. Pat. Nos. 5,998,200, 5,919,689, 6,342,386 B1, which are incorporated herein by reference, utilize microorganisms, spores, and enzymes as additives, singularly or in combination with each other, in coatings, paints, and construction materials. The selection being determined by the characteristics of the resultant microbiological growth, thereby frequently eliminating the adverse affects of other microorganisms that would be detrimental to the substrate.

According to the teachings of U.S. Pat. No. 5,919,689, for example, a coating composition may contain microorganisms and/or hydrolytic enzymes in a binder that is applied to a surface to reduce fouling, surface corrosion, and undesired growth of microorganisms. Among the microorganisms found to be useful in such a coating composition are those that produce at least one amylolytic and/or proteolytic enzyme. Compositions described in this patent may include a polymer resin base, although it is possible to operate without such a base, or a base of a different material. The compositions may be applied as a single coating or as multiple coatings.

The present invention includes the recognition that coatings can achieve enhanced microbial performance where a layering technique is employed. The structures of the present invention are distinguished from the multiple coatings of U.S. Pat. No. 5,919,689 in that multiple layers of the present invention are different: e.g., in terms of dimensions, in terms of ingredients in each layer or different in terms of the amounts of the same ingredients in each layer. While it is recognized that some minor differences may inadvertently occur even when attempting to apply the same coating multiple times, the differences contemplated by this invention are greater than such inadvertent differences. Although the advantages of the layering technique described in this application may be inherent if multiple coatings of the same composition are employed, there was no recognition of those advantages in the '689 patent.

Those skilled in the art are also aware that microorganisms and enzymes have an activity rate that is temperature dependent. See "Dynamic Aspects of Biochemistry," Baldwin, Ernest; Cambridge University Press, 1967, pages 15–17. "Most chemical reactions are influenced by temperature, the reaction velocity increasing with rising and decreasing with falling temperature. Enzyme-catalyzed reactions are no exception to this general rule, but because enzymes are very susceptible to thermal inactivation, the higher the temperature becomes, the more rapidly are the catalytic properties destroyed." Baldwin, Ernest Sc. D. F. I. Biol. Dynamic Aspects of Biochemistry, $5^{th}$ Edition, Cambridge University Press, 1967, p. 15–18. "The catalytic properties of an enzyme are, as a rule, exercised only over a somewhat restricted range of pH. Within this range the activity passes through a maximum of some particular pH, and then falls off again. In its general form, the pH/activity curve of a typical enzyme closely resembles that obtained by plotting the degree of ionization of a simple ampholyte such as glycine against pH. It will be recalled that most of the physical properties of solutions of ampholytes such as proteins and amino-acids, such properties as solubility, osmotic pressure, conductivity, viscosity and so on, pass through either a maximum or a minimum at some particular pH." Id.

One embodiment of this invention involves the process of layering a coating material with microbiological and enzyme additives. This layering produces an increase in the activity of the microorganisms at the interface of the substrate and the environment. The layered material with microbiological additives does not have to be multiple layers of the same material, e.g., coatings or paints, but the layers frequently contain cells, spores, or enzymes singularly or in any combination, and/or a nutrient source. These ingredients can be added to the coating material as such or added in the form of these ingredients absorbed to a substrate such as calcium carbonate, clay, talc, or aluminum stearate. One of the benefits of a layered construction is that not all ingredients that are used in the layered composite are required to be compatible. Incompatible materials, or materials sensitive to different solvents used in forming a layer, can usually be isolated in separate layers. Layers can also be applied in different thicknesses.

Layering can provide a multiplicity of advantages towards the activity of the protective enzymes and microorganisms. This includes a nutritive source for the microorganisms in a layer not exposed to the environment (i.e., seawater), yet excluding the availability of the nutritive source to the "natural" film forming organisms while remaining available for the growth and activity of the protective inoculant added to another layer, e.g., the uppermost layer. Representative examples of a nutrition source include sugars, sugar alcohols, polypeptides, yeast extract, polysaccharides, and hydolsates of complex organic materials. Additionally small molecular salts (i.e., NaCl) which are complimentary to the cell and enzyme activity can optionally be added as adjuvants to the lower layer.

A nutrient source is only one option, but when utilized, it will generally be an internal layer of the total coating substrate rather than at the interface with the environment. Another embodiment of this invention may involve microbiological materials embedded or dissolved in hardened liquids (i.e., solidified resins, paints, coatings, and waterborne coatings) that can translate or mitigate from one layer to another and still retain their reactivity.

Further, embodiments of this invention provide the effect that microbiologic and enzymatic activity is greater than that anticipated if one summed activity of the inoculated additives of the individual layers. In other words, the microbiologic and enzymatic activity can be synergistic, i.e., the sum of the whole activity is greater than the activity sum of the parts. One can measure this by assaying the level of enzymatic activity after each successive addition of the inoculated coating layers. The effect can be achieved with layered material. As an example of this layering, in the construction of recreational boats, microorganisms and spores may be added to the gel coat finish of the hull. Adding nutrient material to a barrier base coat on the inoculated gel coat creates the second layer. The final step is inoculating each of the successive finish coats with enzymes and vegetative cells to complete the process.

While attempting to optimize the application of microorganisms and enzymes as an anti-foulant for underwater surfaces, a particularly successful combination of cells and enzymes (*Bacillus Subtilis*, Pseudomonas and Alpha Amylase) has been discovered. This combination works well in that it breaks down the protein and polysaccharides within the exudates of the settling organisms. Settlement upon a surface begins first with molecular fouling consisting of polysaccharides, proteins, and protein particles. This conditioning film establishes criteria for microfouling which involves bacteria, microalgae, and fungi. Shortly thereafter, macrofouling settlement begins with macroalgae and invertabrates. The use of microorganisms and enzymes often produces a superior protective coating in which diffusion occurs across the layered boundaries yielding activity levels greater than the anticipated combination of inoculated material in each of the layers. In such a system, one community of organisms and/or enzymes can be physically separated from a second community, and still maintain physiological communication. By selecting compatible coating's matrixes, using as criteria, pH ranges, temperature, by products, and effect on the target organism, a system can be constructed which encourages a positive communal relationship, such as hydrolytic activity, between coating material and their microbial/enzyme inhabitants, thereby amplifying the protection of the coating against encroachment by the fouling community.

In the use of coatings, one is constantly concerned with rheology. One of the predominant factors here is the percent of solids within the coating. Conversely, as we develop coatings it may be desirable to load the coating with solids which in the end will not significantly detract from the rheology performance of the coating. The microbiological and enzyme additives in a coating can be reduced in concentration to improve rheology, however, by layering, the coating activity can be greater. The goal is a coating which is usually easier to apply, performs better, and is more effective.

Another embodiment of the invention may involve the addition of nutritional material to an underlayer to provide a source of food for the supportive microorganisms without encouraging the growth of a competing or disruptive fouling community. This process significantly reduces the challenge of adding sufficient amounts of microorganisms, enzymes, and spores to adequately out-compete other bacteria introduced either by chance or residence in the environment of which the coating, substrate, or material will reside or operate. This is accomplished by layering, so that the coating activity can be maintained, or its loss due to reduced concentration in the upper layer is minimized. A constant source of nutrition available to the vegetative cells provides for growth in the colony at a sustained rate without regard to the environment. The quantitative reduction of additives moreover broadens the spectrum of material that can employ this concept. The amount of space available for additives in a coating, as expressed and calculated as a percent of solids, is determined by the chemical characteristics of the coating or substrate material and the desired rheology. Previously it is believed that candidate carriers for the additives were sometimes eliminated because of a spatial shortfall within the chemical structure, thereby directly governing the degree of activity from the additives.

The coating material may include one or more microorganism, although it is possible to practice the invention with such microorganism. Genera of suitable microorganisms include: *Bacillus, Escherichia, Pseudomonas,* yeast (e.g., *Saccharonyces*) fungi (e.g., *Aspergillus*) or other microorganisms known in the art. The microorganisms selected should act in the intended environment to prevent or reduce attachment by unwanted or undesired organisms. The microorganisms chosen should be able to survive and flourish in the environment to which they will be exposed.

The coating materials may include various hydrolytic enzymes, although it is possible to practice the invention without such hydrolytic enzymes. Examples of suitable enzymes include proteases, amylases, cellulases, lyases, hydrolase's, and other hydrolytic enzymes known in the art. The hydrolytic enzymes selected should act to prevent or reduce attachment by unwanted or undesirable organisms. The hydrolytic enzyme should be able to survive and flourish in the environment to which they will be exposed.

Each layer of coating material may include optional ingredients that could affect the properties of the layer and/or the characteristics of an article coated with multiple layers. For example, the coating material may contain a binder that is a polymeric or other coating material such as epoxy resins, polyurethanes, polyesters, acrylics, silicones, copolymers of acrylic and other monomers or fiberglass. It should be understood that the coating material can be in a variety of forms, including paints, pastes, lacquers, laminates, waxes, gells, and glues in addition to other forms known to one skilled in the art. The coating materials may be polymeric, oligomeric, nonomeric, and may contain cross-linking agents or cure promoters as needed. Inorganic salts such as NaCl, Ca $Cl_2$, $MgSO_4$, ammonium salts, and potassium phosphate may be added in a catalytically effective amount as known to those skilled in the art. Additives including preservatives, pigments, dyes, fillers, surfactants and other additives may be added to accomplish known purposes.

Coating materials and multiple layers according to this invention may be applied to any surface to prevent or retard the growth or accumulation of unwanted or undesired organisms on the surface. The methods and compositions may be used on a variety of surfaces, including but not limited to those in a marine environment, a blood system, or exposed to air such as boat hulls, marine markers, bulkheads, pilings, water inlets, floor, roofs, shingles, framing material, fencing, cement structures, and substrate or construction material for medical implant devices. Each layer of coating material may be applied in any desired thickness, but layers are generally in the range of 3 to 4 mils thick. These dimensions are exemplary only since the thickness of any layer will be dependent on several factors such as ingredients in the layer, the number of layers present, the results desired and intended duration of the effects.

In a layered configuration, diffusion of the biological additives occurs when layers of coating material are exposed to, in the presence of, or submerged in a fluid composition thereby increasing the activity of a given concentration of cells without enhancing the growth of the fouling organisms. As most materials have some porosity, the fluid permeates the layered material and the substrate, thereby contributing to the diffusion. But the process does not rely solely upon diffusion. Even in coated material in which the base coat contains additives, and then top coating is without any microbiological additives there was robust activity on the surface. There is apparently an ionic effect much similar to the "bioelectric effect" that potentiates the directional dispersion of the biological additive even in the absence of a fluid substance. See Khoury, A. E. Lam, K., Ellis, B. & Costerton, J. W. (1992) Prevention and Control of Bacterial Infections Associated with Medical Devices. ASA10 Journal, 38, M174–M178. This movement either by diffusion or bioelectric influence creates a concentration of the biological additives at the interface of the substrate and the external environment. The concentration potentiates the biologicals to more rapidly out-complete biologicals from the external environment, thereby avoiding what in most instances is a disruptive influence upon the performance of the substrate.

EMBODIMENTS OF THE INVENTION

The process of the present invention lends itself to many environments where the application of a coating is employed to protect a substrate against unwanted microbial adherence. The durability and minimal permeability of marine coatings present the ultimate challenges for rapid diffusion of biological material to the interface between the protected substrate and the environmental likely to introduce microbial adherence.

These examples demonstrate the advantages of using multiple layers of microbiological enriched antifouling coatings. Coated surfaces impregnated with microorganisms as anti-foulant additives depend on the infusion of nutrients from the sea to support their growth and multiplication. Nutrients to augment the growth of the protective microbial population can be included in the coating. However, since both the indigenous sea community and the protective microorganisms can benefit from the added nutrients, little can be gained by their addition to the underwater surface coating. This does not mean that microbiological material should not be added to the surface, but it does caution against inoculating the layer with material that will benefit indigenous organism that are competing to dominate the interface with the environment.

Certain paints used as underwater surface coatings, while appearing as an impervious barrier to seawater, are sufficiently permeable to allow water-soluble nutrients and microbial products into the coating structure. It is not uncommon to observe proteins and salts as examples of material introduced into a substrate, not necessarily delivered only by water but also by the earth, the air and blood systems of living creatures. This process also aids to diffuse additive material from an undercoated layer to an overcoated surface layer that is exposed to the environment. Likewise, the rate of diffusion is sufficient to support the growth of the microorganisms loaded into the coating exposed to the environment, thereby increasing the size and activity of the colony. In certain embodiments, the surface exposed layer that interfaces with the environment is resultantly enriched with enzymes from internal layers, protecting the surface from being fouled by the environment's biotic population. Unless otherwise indicated, proportions of the ingredients identified in the examples are parts by weight.

EXAMPLE 1

| Materials Used: | |
|---|---|
| Coatings - | New Nautical Coatings<br>2181 24th Way<br>Largo, FL 33771<br>One - Cukote and Monterey |
| Enzymes - | Genecor International<br>200 Meridian Centre Blvd.<br>Rochester, NY 14618-3916<br>Alpha - Amylase 15000L |
| Cells - | Sybron Chemicals Inc.<br>P.O. Box 66<br>Birmingham, NJ 08011<br>SB Concentrate<br>Genesis Technologies International<br>696 Winer Industrial Way<br>Lawrenceville, GA 30045-7600<br>20 × NF (spore suspension)<br>BEC 106 (cell adsorbed to Calcium Carbonate) |

Fiberglass rods were undercoated by brush to approximately 3 mils wet thickness with either New Nautical Cukote, an acrylic copolymer, coating or coating enriched with 0.5% Sigma nutrient broth powder. The rods were dried in air and overcoated with Cukote coating containing 2.0% alpha-amylase and 2.0% vegetative cells adsorbed to calcium carbonate. The overcoat was applied by brush to a thickness of approximately 3 mils wet. The double-coated rods were dried in air and their levels of amylolytic activity determined after 45 minutes immersion in a preheated starch suspension by iodometric titration. All cuprous oxide was removed from the tested coatings and replaced with non-toxic fillers. The test, quantifying the hydrolysis of starch using iodine as a telltale of the process, determined that the enzymes diffused to the surface interface with the environment. Moreover, the quantification of the hydrolysis clearly demonstrated that the activity from a sublayer was greater. The activity is tabulated in Table 1 below.

TABLE 1

| | | % HYDROLYSIS |
|---|---|---|
| TOP COAT | CUKOTE + 2.0% ALPHA-AMYLAYSE + 2.0% VEGETATIVE CELLS | 50 |
| BOTTOM COAT | CUKOTE | |
| TOP COAT | CUKOTE + 2.0% ALPHA-AMYLASE + 2.0% VEGETATIVE CELLS | 90 |
| BOTTOM COAT | CUKOTE + 0.5% NUTRIENT BROTH | |

EXAMPLE 2

Fiberglass rods were undercoated by brush to a wet thickness of 3 mils with New Nautical Monterey coating or Monterey coating enriched with 2.0% Sigma nutrient broth. The rods were dried in air and overcoated by brush to a wet thickness of 3 mils with Monterey coating containing 14% spores and 2% vegetative cells. The double-coated rods were dried in air and their levels of amylolytic activity determined after 45 minutes immersion in a preheated starch suspension by iodometric titration. Again all biocide material was removed from coatings and replaced with nontoxic fillers. The results of the test are tabulated in Table 2 and clearly show that nutrient in a sublayer increase significantly the activity of microbiological additives in separately applied topcoats.

TABLE 2

| | | % HYDROLYSIS |
|---|---|---|
| TOP COAT | MONTEREY COATING + 14% SPORES + 2.0% VEGETATIVE CELLS | 50 |
| BOTTOM COAT | MONTEREY COATING | |
| TOP COAT | MONTEREY COATING + 14% SPORES + 2.0% VEGETATIVE CELLS | 95 |
| BOTTOM COAT | MONTEREY COATING + 2% NUTRIENT BROTH | |

EXAMPLE 3

Fiberglass rods were undercoated by brush to a wet thickness of 3 mils with Monterey paint without biocides but with and without the addition of 2.5% Sigma nutrient broth powder. The rods were dried in air and overcoated by brush to a wet thickness of 3 mils with Cukote coating enriched with a 1.0% mixture of vegetative cells and spores (BEC 110 and 106VBEC) supplied by Genesis Technologies International. The double-coated rods were air-dried and their levels of amylolytic activity determined after 30 minutes immersion in a preheated starch suspension by iodometric titration. The results are tabulated in Table 3 and again clearly demonstrate increased activity derived from the presence of a nutrient source in a sublayer.

TABLE 3

| | | % HYDROLYSIS |
|---|---|---|
| TOP COAT | CUKOTE COATING + 7.0% ALPHA-AMYLASE + 7.0% SPORES + 1.0% VEGETATIVE CELLS | 20 |
| BOTTOM COAT | MONTEREY COATING | |
| TOP COAT | CUKOTE COATING + 7.0% ALPHA-AMYLASE + 7.0% SPORES + 1.0% VEGETATIVE CELLS | 100 |
| BOTTOM COAT | MONTEREY COATING + 2.5% NUTRIENT BROTH | |

EXAMPLE 4

| Materials Used: | |
|---|---|
| Coatings - | New Nautical Inc. Cukote and Monterey Paints |
| Enzymes - | Genecor International Alpha - Amylase (15,000L) |
| Cells - | Genesis Technologies International BEC 106 (vegetative cells adsorbed to calcium carbonate) BEC 110 (spores adsorbed to calcium carbonate) |

Fiberglass rods were undercoated by brush to a wet thickness of 3 mils with either Monterey Paint or with Monterey Paint enriched with nutrient broth (2.5%), vegetative cells (1%) and spores (1.0%). The undercoated rods were top coated by brush to a wet thickness of 3 mils with Cukote Paint enriched with 7.0% alpha-amylase, 7.0% spores and 1.0% vegetative cells. The double-coated rods were dried in air and their levels of amylolytic activity determined by iodometric titration after 45 minutes immersion in a preheated starch suspension. The results are tabulated in Table 4 and demonstrate the added value of inoculating sublayers with microbiological material.

TABLE 4

| | | % HYDROLYSIS |
|---|---|---|
| TOP COAT | CUKOTE COATING + 7.0% ALPHA-AMYLASE + 7.0% SPORES + 1.0% VEGETATIVE CELLS | 30 |
| BOTTOM COAT | MONTEREY COATING | |
| TOP COAT | CUKOTE PAINT + 7.0% ALPHA-AMYLASE +7.0% SPORES + 1.0% VEGETATIVE CELLS | 100 |
| BOTTOM COAT | MONTEREY PAINT + 2.5% NUTRIENT BROTH + 1.0% VEGETATIVE CELLS + 1.0% SPORES | |

EXAMPLE 5

| Materials Used: | |
|---|---|
| Coatings - | U.S. Paint |
| | Undercoating - Primer Hull - Guard W B |
| | Top Coating - G.L.A.F. |
| Enzymes - | Genecor International |
| | Alpha - Amylase 15000L |
| Cells - | Genesis Technologies International |
| | BEC 106V (cells adsorbed to calcium carbonate) |
| | BEC 110 (spores adsorbed to calcium carbonate) |

Fiberglass rods were undercoated by brush to a wet thickness of 3 mils with U.S. Paint Hull-Guard W B coating, a modified epoxy resin, with or without the addition of nutrient broth powder (6%). The rods were dried in air and overcoated by brush to a wet thickness of 3 mils with U.S. Paint G.L.A.F. containing 6% alpha-amylase, 3% BEC 106V (vegetative cells) and 3% BEC 110 (spores) and their levels of alpha-amylolytic activity determined by iodometric titration.

Initially, the activity of the cells and enzymes in both the formulations with and without nutrient broth in the underlayer were of equal activity. However after 72 hours, the activity of the cells and enzymes in contact with the nutrient broth enriched layer increased significantly over that of the cells formulated without nutrient broth powder in the undercoat. The results are tabulated in Table 5.

TABLE 5

| | | % HYDROLYSIS |
|---|---|---|
| TOP COAT | U.S. COATING G.L.A.F. + 6% ALPHA-AMYLASE + 3% BEC 106V + 3% BEC 110 | 20 |
| BOTTOM COAT | U.S. COATING HULL - GUARD W B | |
| TOP COAT | U.S. COATING G.L.A.F. + 6% ALPHA-AMYLASE + 3% BEC 106V + 3% BEC 110 | 100 |
| BOTTOM COAT | U.S. COATING HULL - GUARD W B + 6% NUTRIENT BROTH POWDER | |

EXAMPLE 6

| Materials Used: | |
|---|---|
| Coatings - | U.S. Paint<br>Undercoating - Primer Hull - Guard W B<br>Top Coating - U.S. Antifoul Paint modified with exclusion of all copper |
| Enzymes - | Genecor International<br>Alpha - Amylase 15000L<br>Genesis Technology - Cellulase |
| Cells - | Genesis Technologies International<br>BEC 106V (cells adsorbed to calcium carbonate)<br>BEC 110 (spores adsorbed to calcium carbonate)<br>20 × NF (spores suspension) |

Fiberglass rods were undercoated by brush to a wet thickness of 3 mils with U.S. Paint epoxy primer Hull-Gard ER containing 4.0% each of vegetative cells (BEC 106v) spores (BEC 110) and 20×NF, alpha-amylase and cellulase. The paint mixture was dried in air for 18 hours and overcoated by brush to a wet thickness of 3 mils with U.S. antifoul paint modified by the exclusion of copper which rendered it inert to marine organisms. The rods were examined for their hydrolytic activity after immersion in a starch suspension for 30 minutes. The results are tabulated in Table 6.

TABLE 6

| | | % HYDROLYSIS |
|---|---|---|
| TOP COAT | U.S. PAINT WITHOUT COPPER | 85 |
| BOTTOM COAT | HULL-GUARD + SPORES, CELLS AND ENZYMES | |
| TOP COAT | U.S. PAINT WITHOUT COPPER + SPORES, CELLS AND ENZYMES | 100 |
| BOTTOM COAT | HULL-GUARD | |

EXAMPLE 7

| Materials Used: | |
|---|---|
| Coatings - | NeoCAR( ™) Acrylic Latex 850<br>Union Carbide Corporation<br>Subsidiary of Dow Chemical Corporation<br>39 Old Ridgebury Road<br>Danbury, CT 06817-0001 |
| Enzymes - | Genesis Technologies International - Alpha Amylase<br>Genesis Technologies International - Cellulase |
| Cells - | Genesis Technologies International<br>20 × NF (Spores Suspension)<br>BEC 106V Liquid (derived from dry 106v) |

Fiberglass rods were brush coated to a wet thickness of 3 mils with Dow Acrylic coating containing 20% of a 30:30:30:15 mixture of alpha-amylase: 20×NF: 106V liquid equivalent of 106V: and liquid cellulase. Two through five successive brush coatings of a wet film thickness of 3 mils were applied to four fiberglass rods with a 30-minute drying period between each application. The rods were then assayed for their hydrolytic activity after each coat, using a suspension of corn starch (2 TBL/100 ML water) as their substrate. Hydrolytic activity was measured after immersion in a boiled starch suspension and expressed in terms of viscosity. Viscosity was measured by the addition of a standard weight to the surface of the heated starch suspension and expressed as the reciprocal of the time from the surface of the starch suspension through a measured distance. Activity of the inoculated coatings increased with each successive layer. After the fourth layer the viscosity of the heated starch suspension was not demonstrably reduced since it approached that of water. The kinetics suggests that the velocity of the hydrolytic reaction increased as the enzyme became saturated with its substrate (starch) and then became less active as the substrate became limiting. Moreover the resultant biofilm essentially developed in two dimensions wherein had it been allowed the time to mature in the third dimension, thereby increasing surface area, one would expect further effects of layering beyond the fourth coat.

TABLE 7

| Number of Coats | Hydrolytic Activity |
| --- | --- |
| 0 | 0 |
| 2 | .14 |
| 3 | .49 |
| 4 | 1.9 |
| 5 | 1.9 |

EXAMPLE 8

| Materials Used: | |
| --- | --- |
| Coatings - | U.S. Paints |
| | Undercoating - Primer hull - guard WB |
| | Top Coat Anti-Fouling Base |
| METS Additives | |
| Enzymes - | Genesis Technologies International |
| | Apha Amylase |
| | Cellulase |
| Cells - | Genesis Technologies International |
| | 20 × NF Spores Concentration |
| | BEC 106V (cell absorbed to calcium carbonate) |
| | BEC 110 (Cells absorbed to calcium carbonate) |

Fiberglass rods were brush coated with U.S. Hull Guard primer to a wet film thickness of 3 mils. Two sets of rods were coated with unmodified primer. Two other sets of rods were coated with primer that was augmented with 5 percent sterile water. A final set of rods were coated with primer including the 5 percent sterile water augmentation and saturated with NaCl. All wet film thickness of the primer coats were 3 mils. Next two sets of rods were top coated by brush application to 3 mils wet utilizing U.S. Paints anti-fouling base absent biocides and algaecides. The two sets selected for this treatment involved one set with primer only and the other set with primer augmented with 5 percent sterile water. The remaining three sets of rods were top coated with U.S. anti-fouling base augmented with a 20 percent augmentation of MET'S formulation. In this case the 20 percent was comprised of 35 percent alpha amylase, 35 percent 20×NF, 5 percent 106V, 5 percent 110 and 20 percent cellulose. All primer and topcoat applications were air-dried. The wet film thickness of the brush applications was 3 mils. Our observation clearly disclosed no difference in the water alone augmentation of primer coat but a 2.5 times positive increase in these rods augmented with the NaCl (sodium chloride) in the primer coat.

TABLE 8

| Undercoat | Top Coat | % Hydrolysis |
| --- | --- | --- |
| 1 HGWB | USAF Base | 0 |
| 2 HGWB | USAF Base + 20% "MET'S" | 20 |
| 3 HGWB + 5% H$_2$O | USAF Base + 20% "MET'S" | 20 |
| 4 HGWB + 5% H$_2$O Saturated with NaCl | USAF Base + 20% "MET'S" | 50 |
| 5 HGWB + 50% H$_2$O | USAF Base | 0 |

EXAMPLE 9

| Materials Used: | |
| --- | --- |
| Coatings - | Akzo Nobel Acrylic Resin 17-1267 |
| | Akzo Nobel Resins |
| | 4730 Crittenden Drive |
| | Louisville, KY 40209 |
| Enzymes - | Genesis Technologies International |
| | 696 Winer Industrial Way |
| | Lawrenceville, GA 30045-7600 |
| | Alpha-Amylase |

Two sets of fiberglass rods were brush coated with an Akzo Nobel acrylic resin to a wet thickness of 3 mils. The acrylic resin had an alpha amylase additive mixed at a 10 percent by weight ratio. One set of rods received two coats of resin and the other set of rods received four coats of resin. After air-drying the rods were assayed to qualify their hydrolytic activity. The results in Table 9 demonstrate clearly the level of hydrolytic activity is more than double at four coats as compared to two layers. Multiple layering is an effective method for achieving increased activity without increasing the concentration of biotechnic material. This could be extremely important as the sold content of a coatings formulation strongly influences the performance of the coating before, during and after application.

TABLE 9

| Number of Coats | % Hydrolysis |
| --- | --- |
| 2 × | 30 |
| 4 × | 90 |

EXAMPLE 10

| Materials Used: | |
| --- | --- |
| Coatings - | Akzo Nobel Acrylic Resin 17-1267 |
| | Akzo Nobel Resins |
| | 4730 Crittenden Drive |
| | Louisville, KY 40209 |
| Enzymes - | Alpha Amylase |
| | Genesis Technologies International |
| | 696 Winer Industrial Way |
| | Lawrenceville, GA 30045-7600 |
| Cells - | 106V (Vegetative cells absorbed on calcium carbonate) |
| | 20 × CW (Spores in suspension) |
| | Genesis Technologies International |
| | 696 Winer Industrial Way |
| | Lawrenceville, GA 30045-7600 |

Wooden tongue depressors were brush coated to a wet film thickness of three mils. The bottom coat and two sets had an additive of 10% Alpha-Amylase by weight and the third set was without any additive. All sets were allowed to air-dry overnight. The topcoat of acrylic resin was brush applied to a wet film thickness of 3 mils. One set with additive in the bottom coat received only a resin topcoat. The second set with additive in the bottom coat received topcoat with 20% additive by weight. Half of the additive was 106V and the other half was 20×CW. The third set with no additive in the bottom coat also received the top with 20% additive. Again half the additive was 106V and the other half was 20×CW. After the tongue depressors were allowed to air-dry they were assayed to quantify their amylolytic activity. This was accomplished by immersion of the coated blades in a heated suspension of starch and observing the measure of the starch's loss in suspension as a decrease in viscosity via a viscometer.

TABLE 10

| | | % * Hydrolysis |
|---|---|---|
| Top Coat | AN-17-1267 | 30 |
| Bottom Coat | AN-17-1267 + 10% Alpha-Amylase | |
| Top Coat | AN-17-1267 + 10% 106V + 10% 20 × CW | 69 |
| Bottom Coat | AN-17-1267 + 10% Alpha-Amylase | |
| Top Coat | AN-17-1267 + 10% 106V + 10% 20 × CW | 49 |
| Bottom Coat | AN-17-1267 | |

EXAMPLE 11

| Materials Used: | |
|---|---|
| Coatings - | Alpha Amylase |
| | Genesis Technologies International |
| | 696 Winer Industrial Way |
| | Lawrenceville, GA 30045-7600 |
| Cells - | 106V (Vegetative cells absorbed on calcium carbonate) |
| | 20 × CW (Spores in suspension) |
| | Genesis Technologies International |
| | Lawrenceville, GA 30045-7600 |

Anti-fouling activity by multilayered "MET'S" applied directly to a surface without the benefit of a binder.

Fiberglass rods were coated by immersion and draining of a 50:50 mixture of alpha-amylase and 20×CW (Genesis liquid cold water spore suspension). The rods were dried in an oven for 30 minutes at a temperature of 120°–140° F. The rods were removed, one rod set aside (single coated) and the other four recoated and heated as before. This process was repeated removing one rod after each heating cycle until 5 rods were produced. A sixth rod was used as a control through each heating cycle without the addition of "MET'S". In all 5-coated rods were produced, each having one more coating of "MET'S" than its predecessor (1–5 coatings). The rods were then assayed for their amylolytic activity using a starch suspension containing 2 tablespoons of starch/100 ml water. Heating the coated rods for 2 minutes in just boiled water produced a starch mixture that was progressively more hydrolyzed as the coating number increased. No hydrolysis occurred in the absence of "MET'S" and essentially none occurred with a single coating of "MET'S" (Table). The viscosities were determined by the additions of a drop of liquid from the hydrolyzed mixtures on a vertically held plate and expressed as a rate of travel in a given time. In addition to the increases observed with each successive increase in layering, it appears as if the coatings are not easily lost to the aqueous starch suspensions even when heated and that the non-binder formulation is quite stable and is resistant to degradation due to the temperatures required to achieve liquation of starch suspensions.

TABLE 11

Increased hydrolytic activity by cell and enzymes suspensions in the absence of binder.

| Layer | % Hydrolysis* |
|---|---|
| 1 | 12 |
| 2 | 36 |
| 3 | 50 |
| 4 | 71 |
| 5 | 82 |

*Liquation of a 30% suspension of cornstarch in water.

The concept of layering is applicable likewise to coatings designed with specific functions much the same as the nutritional material. As an example, one can inoculate barrier or bonding primer coating and then topcoat with the coating engineered for aesthetics or desirable operational characteristics. The invention allows one to unload the quantity of inoculants and yet achieve the same effect that higher concentrations yielded.

Embodiments of this invention enable design of materials with physical attributes better able to endure the challenges of harsh environments without major attention to the captivity of the coatings to provide counters for corrosion, rot, prevention of algae and fungus, especially molds in non-assessable areas. The restrictions to which we refer are those of space and environmental considerations when formulating coatings to provide the above protection for long periods of time. It is just these elements, reducing the heavy metal content of coatings and yet improving coating performance that troubles the home construction industry and commercial buildings as well. This invention embodies attributes that allow easier coating designs that provide effective performance against elements of defacement and deterioration related to adverse microbiological influences.

EXAMPLE 12

| Verification of Coating Lamination Benefits |
|---|
| Akzo Nobel Resin<br>2904 Missouri Avenue<br>East St. Louis, IL 62205<br>Product: Acrylic Resin Setalux 17-1267<br>Genesis Alpha Amylase<br>Genesis Technologies International<br>696 Winer Industrial way<br>Lawrenceville, GA 30045-7600<br>Genesis Cells and Spores - Blend 20 × NF CW |

Optimization of Ampholytic Activity by Lamination of Interactive Microbial Enzymes Cells and Spores Fiberglass rods were prepared to accept the acrylic resin coating material. The rod surfaces were sanded with 60 grit paper and wiped with a solvent, acetone, to produce a surface ready for coating. The coating material was applied by brush, approximately to 6 mils wet that yielded a 3 mils dry coating thickness. The coated rods were air dried overnight, approximately 18 hours before applying the second coat or the topcoat of 3 mils dry thickness. The topcoat again was allowed an overnight period to air dry. The activity of the rod surfaces were assessed by preparing a starch solution, which we baseline the viscosity of by means of a viscometer. The prepared rods were submerged in separate solutions for a period of thirty minutes. After the time expired the rods were removed and the viscosity of the solution re-measured. The viscosity was then translated into a percentage of hydrolysis that is documented in Table 12.

Microbial enzymes and cells can be interactive in supporting their activities and growth. In addition to relative concentrations of one component to the other can influence that interaction. However, it is difficult to predict what ratio is optimal, particularly in an inconsistent environment. Laminated layers of enzyme and a mixture of cells and spores are interactive. Enzymes will migrate from one layer of solidified coating to another, and such migration will produce a gradient in the second, upper most layer. Interaction with that gradient results at some point in an optimization of the activity expressed by the cells. This can be of significant advantage in an antifouling coating where high amylolytic activity offers a higher degree of protection.

TABLE 12

|  |  | % * Hydrolysis |
|---|---|---|
| Top Coat | AN-17-1267 | 67 |
| Bottom Coat | AN-17-1267 + 10% Alpha-Amylase | |
| Top Coat | AN-17-1267 + 10% 106V + 10% 20 × NF CW | 100 |
| Bottom Coat | AN-17-1267 + 10% Alpha-Amylase | |
| Top Coat | AN-17-1267 + 10% 106V + 10% 20 × NF CW | 0 |
| Bottom Coat | AN-17-1267 | |

While the invention has been described in connection with certain embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

The invention claimed is:

1. An article having a coating on at least a portion of a surface thereof, said coating comprising at least two layers, wherein at least one first layer comprises at least one microorganism which produces at least one amylolytic or proteolytic enzyme, and wherein at least one second layer, different from said first layer, contains at least one ingredient selected from (a) microorganism that produces at least one amylolytic or proteolytic enzyme, (b) an amylolytic enzyme or (c) proteolytic enzyme, and a (d) nutrient for said microorganism of the at least one first layer.

2. The article of claim 1, wherein the at least one second layer comprises at least one amylolytic or proteolytic enzyme.

3. The article of claim 2, wherein the enzyme in said second layer is different than the enzyme produced by the microorganism.

4. The article of claim 2, wherein the enzyme in said second layer is the same as the enzyme produced by the microorganism.

5. The article of claim 1, wherein the at least one second layer comprises a microorganism that produces at least one amylolytic or proteolytic enzyme.

6. The article of claim 5, wherein the at least one second layer does not include a binder.

7. The article of claim 5, wherein the microorganisms in the first and second layers are the same.

8. The article of claim 7, wherein the microorganism produces at least one enzyme which retards unwanted growth on the surface.

9. The article of claim 1, wherein at least one second layer comprises at least one nutrient for said microorganism of the at least one first layer.

10. The article of claim 9, wherein substantially all of the nutrient for the microorganism is in the at least one second layer.

11. The article of claim 1, wherein the at least one second layer is between the surface of the article and the at least one first layer.

12. The article of claim 1, wherein the at least one first layer further comprises at least one amylolytic or proteolytic enzyme.

13. The article of claim 1, wherein at least one layer includes an inorganic salt.

14. The article of claim 1, wherein at least one layer includes a surfactant.

15. The article of claim 1, wherein at least one layer includes an acrylic binder.

16. The article of claim 1 having a marine surface.

17. The article of claim 1, wherein at least one layer contains vegetative cells absorbed to calcium carbonate, clay, talc, or aluminum stearate.

18. The article of claim 1, wherein at least one layer contains enzymes absorbed to calcium carbonate, clay, talc, or aluminum stearate.

19. The article of claim 1 in a marine environment, a blood system, or exposed to air.

20. An article having a coating on at least a portion of the surface thereof, said coating comprising at least two layers, wherein at least one first layer comprises at least one microorganism which produces at least one amylolytic or proteolytic enzyme, and at least one second layer containing a nutrient for said microorganism.

21. The article of claim 20, wherein at least one layer contains at least one amylolytic or proteolytic enzyme.

22. The article of claim 20, wherein at least one layer contains a binder.

23. The article of claim 22, wherein the binder is an acrylic binder.

24. The article of claim 20, wherein the at least one second layer is between the article and said first layer.

25. The article of claim 20 having a third layer, wherein the first and second layers are between the surface of the article and the third layer.

* * * * *